(12) United States Patent
Scribner et al.

(10) Patent No.: US 7,576,057 B2
(45) Date of Patent: Aug. 18, 2009

(54) CYCLIC PEPTIDES

(75) Inventors: Andrew William Scribner, Durham, NC (US); David Renwick Houck, Cary, NC (US)

(73) Assignee: Scynexis, Inc., Research Triangle Park, NC (US)

( * ) Notice: Subject to any disclaimer, the term of this patent is extended or adjusted under 35 U.S.C. 154(b) by 0 days.

(21) Appl. No.: 11/986,078

(22) Filed: Nov. 19, 2007

(65) Prior Publication Data

US 2008/0171699 A1 Jul. 17, 2008

Related U.S. Application Data

(60) Provisional application No. 60/860,135, filed on Nov. 20, 2006.

(51) Int. Cl.
A61K 38/13 (2006.01)
C07K 7/64 (2006.01)

(52) U.S. Cl. .......................................... 514/11; 530/321

(58) Field of Classification Search ....................... None
See application file for complete search history.

(56) References Cited

U.S. PATENT DOCUMENTS

| | | | |
|---|---|---|---|
| 4,639,434 A | 1/1987 | Wenger et al. |
| 4,703,033 A | 10/1987 | Sebach |
| 4,771,122 A | 9/1988 | Sebach |
| 4,798,823 A | 1/1989 | Witzel |
| 4,814,323 A | 3/1989 | Andrieu et al. |
| 4,885,276 A | 12/1989 | Witzel |
| 4,996,193 A | 2/1991 | Hewitt et al. |
| 5,122,511 A | 6/1992 | Patchett et al. |
| 5,169,773 A | 12/1992 | Rosenthaler et al. |
| 5,214,130 A | 5/1993 | Patchett et al. |
| 5,284,826 A | 2/1994 | Eberle |
| 5,294,604 A | 3/1994 | Nussenblatt |
| 5,489,668 A | 2/1996 | Morrison et al. |
| 5,639,852 A | 6/1997 | Rich et al. |
| 5,846,964 A | 12/1998 | Ozeki |
| 5,863,550 A | 1/1999 | Maeda et al. |
| 5,948,693 A | 9/1999 | Rich et al. |
| 5,948,755 A | 9/1999 | Barriere et al. |
| 5,948,884 A | 9/1999 | Lüchinger |
| 5,965,527 A | 10/1999 | Barriere et al. |
| 5,977,067 A | 11/1999 | Evers et al. |
| 5,981,479 A | 11/1999 | Ko et al. |
| 5,994,299 A | 11/1999 | Barriere et al. |
| 6,254,860 B1 | 7/2001 | Garst |
| 6,350,442 B2 | 2/2002 | Garst |
| 6,444,643 B1 | 9/2002 | Steiner et al. |
| 6,521,595 B1 | 2/2003 | Kim et al. |
| 6,583,265 B1 | 6/2003 | Ellmerer-Müller et al. |
| 6,924,271 B2 | 8/2005 | Averett et al. |
| 6,927,208 B1 | 8/2005 | Wenger et al. |
| 7,196,161 B2 | 3/2007 | Fliri et al. |
| 2004/0077587 A1 | 4/2004 | Sommadossi et al. |
| 2004/0254117 A9 | 12/2004 | Saksena et al. |
| 2006/0025267 A1 | 2/2006 | Gradu |
| 2006/0089301 A1 | 4/2006 | Fliri et al. |
| 2006/0160727 A1 | 7/2006 | Fliri et al. |
| 2007/0173440 A1 | 7/2007 | Houck |

FOREIGN PATENT DOCUMENTS

| | | |
|---|---|---|
| EP | 0 056 782 A1 | 7/1982 |
| EP | 0 414 632 A2 | 7/1990 |
| EP | 0 444 897 A1 | 2/1991 |
| GB | 2 206 119 A | 12/1988 |
| WO | WO 98/28328 | 7/1998 |
| WO | WO 98/28329 | 7/1998 |
| WO | WO 98/28330 | 7/1998 |
| WO | WO 99/32512 A1 | 7/1999 |
| WO | WO 99/67280 A1 | 12/1999 |
| WO | WO 00/01715 A1 | 1/2000 |
| WO | WO 01/47883 A1 | 5/2001 |
| WO | WO 2004/072108 A1 | 8/2004 |
| WO | WO 2005/000308 A2 | 1/2005 |
| WO | WO 2005/021028 A1 | 3/2005 |
| WO | WO 2005/087798 A1 | 9/2005 |
| WO | WO 2006/005610 | 1/2006 |
| WO | WO 2006/038088 A1 | 4/2006 |
| WO | WO 2006/039668 A2 | 4/2006 |
| WO | WO 2006/071619 A1 | 6/2006 |
| WO | WO 2006/071618 A1 | 7/2006 |
| WO | WO 2007/041631 A1 | 4/2007 |
| WO | WO 2007/041632 A2 | 4/2007 |

OTHER PUBLICATIONS

Paechuyse et al. Potent and Selective Inhibition of Hepatitis C Virus . . . Antiviral Research. 2005, vol. 65, p. A41, Abstract No. 28.*

(Continued)

*Primary Examiner*—Jeffrey E Russel
(74) *Attorney, Agent, or Firm*—Jones Day

(57) ABSTRACT

The invention relates to novel cyclic peptide derivatives of general formula (I):

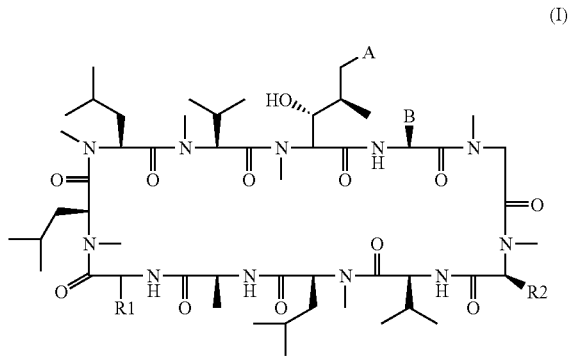

wherein A, B, $R^1$ and $R^2$ are as defined in the specification, pharmaceutically acceptable salts thereof, and their use as pharmaceuticals, in particular for the treatment of hepatitis C virus.

20 Claims, No Drawings

OTHER PUBLICATIONS

European Patent Office, Standard Search Report, issued Sep. 10, 2007, for Application No. RS 115759; filed: Nov. 20, 2006.

Baumgrass et al., 2004, "Substitution in Position 3 of Cyclosporin A Abolishes the Cyclophilin-mediated Gain-of-function Mechanism but Not Immunosuppression," Journal of Biological Chemistry, vol. 279(4):2470-2479.

Billich et al., 1995, "Mode of Action of SDZ NIM 811, a Nonimmunosuppressive Cyclosporin A Analog with Activity Against Human Immunodeficiency Virus (HIV) Type 1: Interference with HIV Protein-Cyclophilin A Interactions," Journal of Virology, vol. 69(4):2451-2461.

Borel et al., 1977, "Effects of the New Anti-Lymphocytic Peptide Cyclosporin A in Animals," Immunology, vol. 32:1017-1025.

Chan, et al., 2004, "Discovery of Thiophene-2-Carboxylic Acids as Potent Inhibitors of HCV NS5B Polymerase and HCV Subgenomic RNA Replication. Part 1: Sulfonamides," Bioorganic & Medical Chemistry Letters, 14:793-796.

Chan, et al., 2004, "Discovery of Thiophene-2-Carboxylic Acids as Potent Inhibitors of HCV NS5B Polymerase and HCV Subgenomic RNA Replication. Part 2: Tertiary Amides," Bioorganic & Medicinal Chemistry Letters, 14:797-800.

Colucci, et al., 1990, "Synthesis of $_D$-Lysine-cyclosporine A. Further Characterization of BOP-Cl in the 2-7 Hexapeptide Fragment Synthesis," J. Org. Chem., vol. 55:2895-2903.

Cotler, Scott J., et al., 2003-04, "A Pilot Study of the Combination of Cyclosporin A and Interferon Alfacon-1 for the Treatment of Hepatitis C in Previous Nonresponder Patients," Journal of Clinical Gastroenterology, vol. 36(4):352-355.

Cruz et al., 2000, "Immunosuppressive and Nonimmunosuppressive Cyclosporine Analogs Are Toxic to the Opportunistic Fungal Pathogen *Cryptococcus neoformans* via Cyclophilin-Dependent Inhibition of Calcineurin," Antimicrobial Agents and Chemotherapy, vol. 44(1):143-149.

Dhanak, et al., 2002, "Identification and Biological Characterization of Heterocyclic Inhibitors of the Hepatitis C Virus RNA-Dependent RNA Polymerase," Journal of Biological Chemistry, vol. 277(41):38322-38327.

DiMarco, et al., 2005, "Interdomain Communication in Hepatitis C Virus Polymerase Abolished by Small Molecule Inhibitors Bound to a Novel Allosteric Site," Journal of Biological Chemistry, vol. 280(33):29765-29770.

Eberle et al., 1994, "Cyclosporin A: Regioselective Ring Opening and Fragmentation Reactions via Thioamides. A Route to Semisynthetic Cyclosporins," J. Org. Chem., vol. 59:7249-7258.

Evers et al., 2003, "Synthesis of Non-Immunosuppressive Cyclophilin-Binding Cyclosporin A Derivatives as Potential Anti-HIV-1 Drugs," Bioorganic & Medicinal Chemistry Letters, vol. 13(24):4415-4419.

Gu, et al., 2003, "Arresting Initiation of Hepatitis C Virus RNA Synthesis Using Heterocyclic Derivatives," Journal of Biological Chemistry, vol. 278(19):16602-16607.

Hansson et al., 2004, "The Nonimmunosuppressive Cyclosporin Analogs NIM811 and UNIL025 Display Nanomolar Potencies on Permeability Transition in Brain Derived Mitochondria," Journal of Bioenergetics and Biomembranes, 36(4):407-413.

Hosmans, et al., 2004, "Isatoribine, A Toll-Like Receptor 7 Agonist, Significantly Reduced Plasma Viral Load in a Clinical Proof-of-Concept Study in Patients with Chronic Hepatitis C Virus Infection," Hepatology, vol. 40:(4), Suppl. 1, Oct. 2004, 282A, No. 270.

Hubler et al., 2000, "Synthetic Routes to NEtXaa[4]-Cyclosporin A Derivatives a Potential Anti-HIV I Drugs," Tetrahedron Letters, 41(37):7193-7196.

Inoue, K. et al., 2003, "Combined Interferon Alpha2b and Cyclosporin A in the Treatment of Chronic Hepatitis C: Controlled Trial," Journal of Gastroenterology, Springer Verlag, Tokyo, JP, vol. 38(6):567-572.

Inoue et al., 2005, "Interferon Combined with Cyclosporin Treatment as an Effective Countermeasure Against Hepatitis C Virus Recurrences in Liver Transplant Patients with End-Stage Hepatitis C Virus Related Disease," Transplantation Proceedings, 37(2):1233-1234.

Kallen et al., 1997, "12 Cyclosporins: Recent Development in Biosynthesis, Pharmacology and Biology, and Clinical Applications," Biotechnology, 2$^{nd}$ Ed. Completely Revised Edition, vol. 7, pp. 535-591.

Lamarre, et al., 2003, "An NS3 Protease Inhibitor with Antiviral Effects in Humans Infected with Hepatitis C Virus," Nature, vol. 426:186-189.

LaPlante, et al., 2004, "Binding Mode Determination of Benzimidazole Inhibitors of the Hepatitis C Virus RNA Polymerase by a Structure and Dynamics Strategy," Angew. Chem. Int., Ed. Engl., vol. 43:4306-4311.

Lee, et al., 2003, "Molecular Basis for the Immunostimulatory Activity of Guanine Nucleoside Analogs: Activation of Toll-Like Receptor 7," PNAS, USA, vol. 100(11):6646-6651.

Lin, et al., 2005, "In Vitro Studies of Cross-Resistance Mutations Against Two Hepatitis C Virus Serine Protease Inhibitors, VX-950 and BILN 2061," Journal of Biological Chemistry, vol. 280(44):36784-36791.

Loor et al., 2002, "Cyclosporins: Structure-Activity Relationships for the Inhibition of the Human MDR1 P-Glycoprotein ABC Transporter," J. Med. Chem., vol. 45:4598-4612.

Loor et al., 2002, Cyclosporins: Structure-Activity Relationships for the Inhibition of the Human FPR1 Formylpeptide Receptor, J. Med. Chem., vol. 45:4613-4628.

Love, et al., 2003, "Crystallographic Identification of a Noncompetitive Inhibitor Binding Site on the Hepatitis C Virus NS5B RNA Polymerase Enzyme," Journal of Virology, vol. 77(13):7575-7581.

Ko et al., 1997, "Solid-Phase Total Synthesis of Cyclosporine Analogues," Helvetica Chimica Acta, vol. 80:695-705.

Masereeuw et al., 2000, "Endothelin B Receptor-Mediated Regulation of ATP-Driven Drug Secretion in Renal Proximal Tubule," Molecular Pharmacology, vol. 57:59-67.

Nakagawa et al., 2004, "Specific Inhibition of Hepatitis C Virus Replication by Cyclosporin A," Biochemical and Biophysical Research Comm., vol. 313:42-47.

Nelson et al., 1993, "Immunosuppressive Activity of [MeBm$_2$t]-, $_D$-Diaminobutyryl-8-, and $_D$-Diaminopropyl-8-Cyclosporin Analogues Correlates with Inhibition of Calcineurin Phosphatase Activity," Journal of Immunology, vol. 150(6):2139-2147.

Nguyen et al., 2003, "Resistance Profile of a Hepatitis C Virus RNA-Dependent RNA Polymerase Benzothiadiazine Inhibitor," Antimicrobial Agents and Chemotherapy, vol. 47(11):3525-3530.

Olsen, et al., 2004, "A 7-Deaza-Adenosine Analog is a Potent and Selective Inhibitor of Hepatitis C Virus Replication with Excellent Pharmacokinetic Properties," Antimicrobial Agents and Chemotherapy, vol. 48(10):3944-3953.

Quesniaux et al., 1987, "Cyclophilin binds to the Region of Cyclosporine Involved in its Immunosuppressive Activity," Eur. J. Immunol., vol. 17:1359-1365.

Quesniaux et al., 1987, "Fine Specificity and Cross-Reactivity of Monoclonal Antibodies to Cyclosporine," Molecular Immunology, vol. 24(11):1159-1168.

Randall, et al., 2003, "Clearance of Replicating Hepatitis C Virus Replicon RNAs in Cell Culture by Small Interfering RNAs," PNAS, vol. 100(1):235-240.

Rüegger et al., 1976, "Cyclosporin A, a Peptide Metabolite from *Trichoderma polysporum* (Link ex Pers.) *Rifai*, with a Remarkable Immunosuppressive Activity," Helvetica Chimica Acta, vol. 59(4) No. 112, pp. 1075-1092.

Schetter, et al., 2004, "Toll-Like Receptors Involved in the Response to Microbial Pathogens: Development of Agonists for Toll-Like Receptor 9," Current Opinion in Drug Discovery & Development, vol. 7(2):204-210.

Schneider et al., 1994, "Human Cyclophilin C: Primary Structure, Tissue Distribution, and Determination of Binding Specificity for Cyclosporins," Biochemistry, vol. 33:8218-8224.

Schote, et al., 2002, "Interactions of Cyclosporines with Lipid Membranes as Studied by Solid-State Nuclear Magnetic Resonance Spectroscopy and High-Sensitivity Titration Calorimetry," Journal of Pharmaceutical Sciences, vol. 91(3):856-867.

Shimotohno E.A. et al., 2004, "Inhibitory Role of Cyclosporin A and its Derivatives on Replication of Hepatitis C Virus," vol. 4(s8):334-335; Abstract No. 648.

Sigal et al., 1991, "Is Cyclophilin Involved in the Immunosuppressive and Nephrotoxic Mechanism of Action of Cyclosporin A?," J. Exp. Med., vol. 173:619-628.

Simmonds, P., 2001, "The Origin and Evolution of Hepatitis Viruses in Humans," *Journal of General Virology*, vol. 82:693-712.

Simmonds, P., 2004, "Genetic Diversity and Evolution of Hepatitis C Virus—15 Years On," *Journal of General Virology*, vol. 85:3173-3188.

Summa, V., 2005, "VX-950 Vertex/Mitsubishi," *Current Opinion in Investigational Drugs*, vol. 6(8):831-837.

Takeda, et al., 2003, "Toll-Like Receptors," *Annual Review Immunology*, vol. 21:335-376.

Tomei, et al., 2003, "Mechanisms of Action and Antiviral Activity of Benzimidazole-Based Allosteric Inhibitors of the Hepatitis C Virus RNA-Dependent RNA Polymerase," *Journal of Virology*, vol. 77(24)13225-13231.

Tomei, et al., 2004, "Characterization of the Inhibition of Hepatitis C Virus RNA Replication by NonNucleosides," *Journal of Virology*, vol. 78(2):938-946.

Traber et al., 1982, "Isolation and Structure Determination of the New Cyclosporins E, F, G. H, and I," Helvetica Chimica Acta, vol. 65(5), No. 162, pp. 1655-1677.

Tung et al., 1989, "Synthesis and Biological Properties of a High Specific Activity Radioiodinated, Photolabile Cyclosporine," UCLA Symp. Mol. Cell. Biol., New Ser. vol. 86:321-335.

Vollenbroeker et al., 2003, "Receptor Assay Based on Surface Plasmon Resonance for the Assessment of the Complex Formation Activity of Cyclosporin A and its Metabolites," Intl. Journal of Clinical Pharmacology and Therapeutics, vol. 41(6):248-260.

Wang, et al., 2003, "Non-Nucleoside Analogue Inhibitors Bind to an Allosteric Site on HCV NS5B Polymerase," *Journal of Biological Chemistry*, vol. 278(11):9489-9495.

Watashi et al., 2003, "Cyclosporin A Suppresses Replication of Hepatitis C Virus Genome in Cultured Hepatocytes," Hepatology, vol. 38(5):1282-1288.

Watashi, et al., 2005, "Current Approaches for Developing New Anti-HCV Agents and Analyses of HCV Replication Using Anti-HCV Agents," *Virus*, vol. 55(1):105-110.

Wenger et al., 1994, "The 3D Structure of a Cyclosporin Analogue in Water is Nearly identical to the Cyclophilin-Bound Cyclosporin Conformation," FEBS Letters, vol. 340:255-259.

Xia et al., 2005, "Inhibitory Effect of Cyclosporine A on Hepatitis B Virus Replication in Vitro and its Possible Mechanisms," *Hepatobiliary & Pancreatic Diseases International*, 4(1):18-22.

Yoshiba, M. et al., 1995, "Interferon and Cyclosporin A in the Treatment of Fulminant Viral Hepatitis," *Journal of Gastroenterology*, Springer Verlag, Tokyo, JP, vol. 30:67-73.

Ziegler et al., 1990, "Cyclosporin Binding to a Protein Component of the Renal $Na^+$-$_D$-Glucose Contransporter," J. Biol. Chem., vol. 265(6):3270-3277.

ISA/US PCT International Search Report dated Jul. 25, 2008, for International Application No. PCT/US2007/24128, filed Nov. 19, 2007.

ISA/US PCT Written Opinion of the International Searching Authority dated Jul. 25, 2008, for International Application No. PCT/US2007/24128, filed Nov. 19, 2007.

Debio Pharm Press Release, New Data Presented on Debiopharm's Debio-25 at the 11th International Symposium on Hepatitis C Virus and Related Viruses in Heidelberg, Germany, Oct. 6, 2004.

Wartburg, A.V., et al., 1988, "Cyclosporins, Fungal Metabolites with Immunosupressive Activities," *Progress in Medicinal Chemistry*, 25:1-33, p. 8, Eds. Ellis, G.P. and West, G.B., Elsevier Science Publishers B.V., New York, N.Y.

\* cited by examiner

US 7,576,057 B2

CYCLIC PEPTIDES

This application claims priority to U.S. provisional application Ser. No. 60/860,135 filed on Nov. 20, 2006, entitled "NOVEL COMPOUNDS". The disclosure of the above referenced application is incorporated by reference herein.

FIELD OF THE INVENTION

This invention relates to novel cyclosporine derivatives, compositions containing them, processes for their preparation, intermediates in their synthesis, and their use as therapeutics, for example as antiviral agents.

BACKGROUND OF THE INVENTION

In 1989, a main causative virus of non-A non-B post-transfusion hepatitis was found and named hepatitis C virus (HCV). Since then, several types of hepatitis viruses have been found besides type A, type B and type C, wherein hepatitis caused by HCV is called hepatitis C. The patients infected with HCV are considered to involve several percent of the world population, and the infection with HCV characteristically becomes chronic.

HCV is an envelope RNA virus, wherein the genome is a single strand plus-strand RNA, and belongs to the genus Hepacivirus of Flavivirus (from The International Committee on Taxonomy of Viruses, International Union of Microbiological Societies). Of the same hepatitis viruses, for example, hepatitis B virus (HBV), which is a DNA virus, is eliminated by the immune system and the infection with this virus ends in an acute infection except for neonates and infants having yet immature immunological competence. In contrast, HCV somehow avoids the immune system of the host due to an unknown mechanism. Once infected with this virus, even an adult having a mature immune system frequently develops persistent infection.

When chronic hepatitis is associated with the persistent infection with HCV, it advances to cirrhosis or hepatic cancer in a high rate. Enucleation of tumor by operation does not help much, because the patient often develops recurrent hepatic cancer due to the sequela inflammation in non-cancerous parts.

Thus, an effective therapeutic method of treating or controlling hepatitis C is desired. Apart from the symptomatic therapy to suppress inflammation with an anti-inflammatory agent, the development of a therapeutic agent that reduces HCV to a low level free from inflammation and that eradicates HCV has been strongly demanded. An optimal therapeutic agent would provide a virologic response classified as a "sustained virologic response," which is defined as undetectable levels of virus in blood six months or more after completing hepatitis C therapy.

At present, a treatment with interferon, as a single agent or in combination with ribavirin, is the only effective method known for the eradication of HCV. However, interferon can eradicate the virus in only about one-third of the patient population. For the rest of the patients, it has no effect or provides only a temporary effect. Therefore, an anti-HCV drug to be used in the place of or concurrently with interferon is awaited in great expectation.

Cyclosporine A is well known for its immunosuppressive activity and a range of therapeutic uses, including antifungal, anti-parasitic, and anti-inflammatory as well as anti-HIV activity. Cyclosporine A and certain derivatives have been reported as having anti-HCV activity, see Watashi et al., Hepatology, 2003, Volume 38, pp 1282-1288, Nakagawa et al., Biochem. Biophys. Res. Commun. 2004, Volume 313, pp 42-7, and Shimotohno and K. Watashi, 2004 American Transplant Congress, Abstract No. 648 (American Journal of Transplantation 2004, Volume 4, Issue s8, Pages 1-653). Cyclosporine derivatives having HCV activity are known from International Publication Nos. WO2005/021028, WO2006/039668 and WO2006/038088.

Cyclosporines substituted in the 8-position by a group other than (D)-Alanine are known from EP0056782, EP0414632, EP 0444897, U.S. Pat. Nos. 4,639,434 and 5,214,130, PCT publication No. WO2004/072108. These compounds are described as having immunosuppressive and/or anti-inflammatory properties. Schote et al, Journal of Pharmaceutical Sciences, March 2002, Volume 91, No. 3 pages 856-867 describes a cyclosporine in which the D-Alanine at the 8-position is replaced by the hydrochloride salt of D-2,3 diaminopropionic acid. Cruz et al, Antimicrobial agents and Chemotherapy, January 2000, Volume 44, No. 1, pages 143-149 describes a cyclosporine in which the D-Alanine in the 8-position is substituted by acetylamino having activity against fluconozole-sensitive and resistant *Cryptoccus neoformans* isolates (a fungal pathogen). Ko et al, Helvetica Chimica Acta, 1997, Volume 80, No. 3, pages 695-705 describes immunosuppressive cyclosporines in which the D-Alanine in the 8-position is replaced by D-Asparagine and D-Glutamine. Sigal et al, The Journal of Experimental Medicine, 1991, Volume 173, pages 619-628 describes a cyclosporin analogue substituted in the 8-position. D-alanine at the 8-position was replaced by both D-2,3-diaminopropionic acid and D-2,4-diaminobutyric acid in Journal of Immunology, 1993, Volume 50, page 2139 (although it appears that these were named incorrectly in this paper as D-1,3-diaminopropionic acid and D-1,4-diaminobutyric acid, respectively. Immunosuppressive activity was reported in this paper.

Colucci et al, J. Org. Chem., 1990, Volume 55, page 2985-2903 describes the synthesis of [D-lysyl]$^8$cyclosporine, which is also described by Loor et al in J. Med, Chem. 2002, Volume 45, pages 4598-4612 and pages 4613-4628 and by Billich et al, Journal of Virology, 1995, Volume 69, No. 4, pages 2451-2461. In particular, Billich et al states that [D-lysyl]$^8$cyclosporine does not inhibit antiviral activity when tested against HIV-1. Surprisingly it has been found that [D-lysyl]$^8$cyclosporine does have antiviral activity against HCV.

In one aspect the present invention seeks to provide cyclosporine derivatives having activity against HCV.

In a further aspect the present invention seeks to provide novel cyclosporine derivatives having activity against HCV with an improved safety margin (i.e. the difference between the dose level of compound required to provide effective control of HCV and the dose levels producing toxicity).

In a further aspect the present invention seeks to provide cyclosporine derivatives having activity against both HCV and HIV.

SUMMARY OF THE INVENTION

In one aspect the invention provides cyclosporine derivatives substituted in the 8-position by an aliphatic hydrocarbon group bearing at least one nitrogen atom, such as compounds of general formula (I):

(I)

[chemical structure diagram of cyclosporine derivative with substituents A, B, R1, R2]

wherein:

A represents (E) —CH=CHCH$_2$R or —CH$_2$CH$_2$CH$_2$R, wherein R represents hydrogen, —SH, thioalkyl, carboxyl or alkoxycarbonyl;

B represents methyl, ethyl, 1-hydroxyethyl, isopropyl or n-propyl;

$R^1$ represents:
  straight- or branched-chain alkyl containing from one to six carbon atoms, substituted by one or more groups $R^3$ which may be the same or different;
  straight- or branched-chain alkenyl or alkynyl containing from two to six carbon atoms substituted by one or more groups $R^3$ which may be the same or different;
  or cycloalkyl containing from three to six carbon atoms optionally substituted by one or more groups $R^3$ which may be the same or different;

$R^2$ represents isobutyl or 2-hydroxyisobutyl;

$R^3$ is selected from the group consisting of —NR$^4$R$^5$, —C(=O)NR$^4$R$^5$ and —C(=NR$^6$)NR$^4$R$^5$;

$R^4$ and $R^5$, which may be the same or different, each represent:
  hydrogen;
  straight- or branched-chain alkyl containing from one to six carbon atoms;
  straight- or branched-chain alkenyl or alkynyl containing from two to four carbon atoms;
  cycloalkyl containing from three to six carbon atoms optionally substituted by straight- or branched-chain alkyl containing from one to six carbon atoms;
  or $R^4$ and $R^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
  or a group —COR$^7$;

$R^6$ represents hydrogen, straight- or branched-chain alkyl containing from one to six carbon atoms, cyano, alkylsulfonyl, sulfonamide or nitro;

$R^7$ represents:
  straight- or branched-chain alkyl containing from one to six carbon atoms optionally substituted with one or more halogen atoms;
  straight- or branched-chain alkenyl or alkynyl containing from two to four carbon atoms;
  cycloalkyl containing from three to six carbon atoms optionally substituted by straight- or branched-chain alkyl containing from one to six carbon atoms;
  or aryl;

or pharmaceutically acceptable salts thereof; with the proviso that (a) the compound is not [D-lysyl]$^8$cyclosporine; and (b) when $R^1$ is —CH$_2$R$^3$ or —CH$_2$CH$_2$R$^3$ then $R^3$ is not amino or —C(=O)NH$_2$.

The compound of formula (I) which is [D-lysyl]$^8$cyclosporine and compounds of formula (I) in which $R^1$ is —CH$_2$R$^3$ or —CH$_2$CH$_2$R$^3$ and $R^3$ is amino or —C(=O)NH$_2$ are known from the literature and do not form part of the invention per se, but their use to treat or prevent HCV does form part of the invention.

In certain cases the substituents A, B, $R^1$ and $R^2$ may contribute to optical and/or stereoisomerism. All such forms are embraced by the present invention.

Mention may be made, as examples of pharmaceutically acceptable salts, of the salts with alkali metals, e.g., sodium, potassium or lithium, or with alkaline-earth metals, e.g., magnesium or calcium, the ammonium salt or the salts of nitrogenous bases, e.g., ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine.

DETAILED DESCRIPTION OF THE PREFERRED EMBODIMENTS

Definitions

When referring to the compounds and complexes of the invention, the following terms have the following meanings unless indicated otherwise.

"Cyclosporine" refers to any cyclosporine compound known to those of skill in the art, or a derivative thereof. See e.g., Ruegger et al., 1976, Helv. Chim. Acta. 59:1075-92; Borel et al., 1977, Immunology 32:1017-25; the contents of which are hereby incorporated by reference in their entireties. Exemplary compounds of the invention are cyclosporine derivatives. Unless noted otherwise, a cyclosporine described herein is a cyclosporine A, and a cyclosporine derivative described herein is a derivative of cyclosporine A.

The cyclosporine nomenclature and numbering systems used hereafter are those used by J. Kallen et al., "Cyclosporins: Recent Developments in Biosynthesis, Pharmacology and Biology, and Clinical Applications", Biotechnology, second edition, H.-J. Rehm and G. Reed, ed., 1997, p 535-591 and are shown below:

| Position | Amino acid in cyclosporine A |
| --- | --- |
| 1 | N-Methyl-butenyl-threonine (MeBmt) |
| 2 | [alpha]-aminobutyric acid (Abu) |
| 3 | Sarcosine (Sar) |
| 4 | N-Methyl-leucine (MeLeu) |
| 5 | Valine (Val) |
| 6 | N-Methyl-leucine (MeLeu) |
| 7 | Alanine (Ala) |
| 8 | (D)-Alanine [(D)-Ala] |
| 9 | N-Methyl-leucine (MeLeu) |
| 10 | N-Methyl-leucine (MeLeu) |
| 11 | N-Methyl-valine (MeVal) |

This corresponds to the saturated ring carbon atoms in the compounds of formula (I) as shown below:

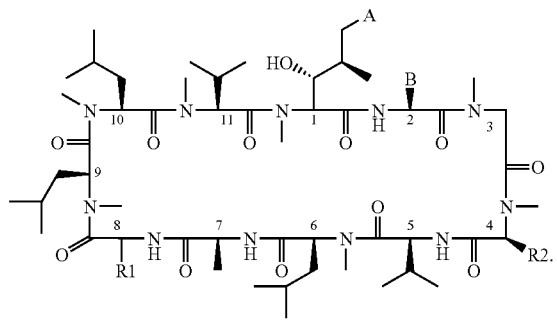

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"N-Alkylamino" refers to the group alkyl-NR'—, wherein R' is selected from hydrogen and alkyl.

"Alkylsulfonyl" refers to a radical —S(=O)$_2$alkyl, where alkyl is as defined herein.

"Alkoxycarbonyl" refers to a radical —C(=O)-alkoxy, where alkoxy is as defined herein.

"Amino" refers to the radical —NH$_2$.

"Aryl" refers to an optionally substituted aromatic hydrocarbon radical, for example phenyl.

"Arylamino" refers to the group aryl-NR'—, wherein R' is selected from hydrogen, aryl and heteroaryl.

"Bmt" refers to 2(S)-amino-3(R)-hydroxy-4(R)-methyl-6 (E)-octenoic acid.

"Carboxyl" refers to the radical —C(=O)OH.

"N,N-Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Halogen" or "halo" refers to chloro, bromo, fluoro or iodo.

"Heteroaryl" refers to an optionally substituted saturated or unsaturated heterocyclic radical. Generally the heterocyclic ring contains from 4 to 7 ring atoms, e.g. 5 or 6 ring atoms. Examples of heteroaryl include thienyl, furyl, pyrrolyl, oxazinyl, thiazinyl, pyrazinyl, pyrimidinyl, pyridazinyl, thiazolyl, oxazolyl, imidazolyl, morpholinyl, pyrazolyl and tetrahydrofuryl.

"Hydroxy" refers to the radical —OH.

"Nitro" refers to the radical —NO$_2$.

"Thioalkyl" refers to the group —SR where R is alkyl. Examples include, but are not limited to, methylthio, ethylthio, propylthio, butylthio, and the like.

"Pharmaceutically acceptable salt" refers to any salt of a compound of this invention which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl) benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalene-sulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound of the present invention or a salt thereof that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, Angew. Chem. 78:413-447, Angew. Chem., Int. Ed. Engl. 5:385-414 (errata: Angew. Chem., Int. Ed. Engl. 5:511); Prelog and Helmchen, 1982, Angew. Chem. 94:614-631, Angew. Chem. Internat. Ed. Eng. 21:567-583; Mata and Lobo, 1993, Tetrahedron: Asymmetry 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds of this invention may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon treatment with base.

In certain embodiments, the compounds of the invention are "stereochemically pure". A stereochemically pure compound or has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

"Sarcosine" or "Sar" refers to the amino acid residue known to those of skill in the art having the structure —N(Me)CH$_2$C(=O)—. Those of skill in the art might recognize sarcosine as N-methyl glycine.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a monkey such as a cynomolgous monkey, a chimpanzee and a human), and more preferably a human. In another embodiment, the subject is a farm animal (e.g., a horse, a cow, a pig, etc.) or a pet (e.g., a dog or a cat). In a preferred embodiment, the subject is a human.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound of the invention. In certain other embodiments, the term "therapeutic agent" refers does not refer to a compound of the invention. Preferably, a therapeutic agent is an agent that is known to be useful for, or has been or is currently being used for the treatment, management, prevention, or amelioration of a disorder or one or more symptoms thereof.

"Therapeutically effective amount" means an amount of a compound or complex or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound of the invention. In certain other embodiments, the term "prophylactic agent" does not refer a compound of the invention. Preferably, a prophylactic agent is an agent which is known to be useful for, or has been or is currently being used to prevent or impede the onset, development, progression and/or severity of a disorder.

As used herein, the terms "prevent", "preventing" and "prevention" refer to the prevention of the recurrence, onset, or development of one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the phrase "prophylactically effective amount" refers to the amount of a therapy (e.g., prophylactic agent) which is sufficient to result in the prevention of the development, recurrence or onset of one or more symptoms associated with a disorder, or to enhance or improve the prophylactic effect(s) of another therapy (e.g., another prophylactic agent).

The term "label" refers to a display of written, printed or graphic matter upon the immediate container of an article, for example the written material displayed on a vial containing a pharmaceutically active agent.

The term "labeling" refers to all labels and other written, printed or graphic matter upon any article or any of its containers or wrappers or accompanying such article, for example, a package insert or instructional videotapes or DVDs accompanying or associated with a container of a pharmaceutically active agent.

In certain embodiments, A represents (E) —CH═CHCH$_2$R. In further embodiments, A represents —CH$_2$CH$_2$CH$_2$R. In a preferred embodiment, A represents (E) —CH═CHCH$_2$R.

In one embodiment, R represents hydrogen.

In one embodiment, B represents ethyl, 1-hydroxyethyl, isopropyl or n-propyl. In another embodiment B represents ethyl.

In one embodiment the group $R^1$ is the (D) isomer.

In one embodiment $R^1$ represents straight- or branched-chain alkyl containing from one to six carbon atoms, substituted by one group $R^3$. In another embodiment $R^1$ represents straight-chain alkyl containing from one to four carbon atoms substituted by a group $R^3$. In a further embodiment $R^1$ represents straight- or branched-chain alkyl containing from two to six carbon atoms, substituted by one group $R^3$.

In certain embodiments $R^2$ represents isobutyl. In other embodiments $R^2$ represents 2-hydroxyisobutyl.

In one embodiment $R^3$ represents —NR$^4$R$^5$. In another embodiment $R^3$ represents —C(═O)NR$^4$R$^5$. In a further embodiment $R^3$ represents —C(═NR$^6$)NR$^4$R$^5$.

In a further embodiment $R^4$ and $R^5$, which may be the same or different, represent hydrogen or straight- or branched-chain alkyl containing from one to six carbon atoms. In a further embodiment $R^4$ and $R^5$ represent hydrogen or methyl.

In a further embodiment $R^7$ represents:
straight- or branched-chain alkyl containing from one to six carbon atoms optionally substituted with one or more halogen atoms; straight- or branched-chain alkenyl or alkynyl containing from two to four carbon atoms;
or cycloalkyl containing from three to six carbon atoms optionally substituted by straight- or branched-chain alkyl containing from one to six carbon atoms.

In a further embodiment provides compounds of formula (I) above in which A represents (E) —CH═CHCH$_2$R; B represents ethyl; R represents hydrogen; $R^1$ represents straight-chain alkyl containing from one to six carbon atoms substituted by a group $R^3$; $R^2$ represents isobutyl; $R^3$ represents —NR$^4$R$^5$; and $R^4$ and $R^5$ represent hydrogen or straight- or branched-chain alkyl containing from one to six carbon atoms (e.g. methyl).

Particularly preferred compounds of the invention include:
1. [(N,N-ε-Dimethyl)-D-lysyl]$^8$cyclosporine; and 2. [D-Lysyl]$^8$cyclosporine.

The numbers 1 and 2 are used to describe these compounds hereafter.

The following are further representative compounds of formula (I), in which A is (E) —CH═CHCH$_3$ and B is ethyl. Unless otherwise stated, $R^1$ is present in (D) stereochemistry:

| $R^1$ | $R^2$ |
|---|---|
| CH$_2$N(CH$_3$)$_2$ | Isobutyl |
| CH$_2$CH$_2$N(CH$_3$)$_2$ | Isobutyl |
| CH$_2$CH$_2$CH$_2$N(CH$_3$)$_2$ | Isobutyl |
| CH$_2$CH$_2$CH$_2$CH$_2$NHCH$_3$ | Isobutyl |
| CH$_2$CH$_2$CH$_2$CH$_2$N(CH$_3$)$_2$ | Isobutyl |
| L-CH$_2$CH$_2$CH$_2$CH$_2$NH$_2$ | Isobutyl |
| L-CH$_2$CH$_2$CH$_2$CH$_2$N(CH$_3$)$_2$ | Isobutyl |
| CH$_2$CH$_2$CH$_2$CH$_2$NHCH$_2$CH$_3$ | Isobutyl |
| CH$_2$CH$_2$CH$_2$CH$_2$N(CH$_2$CH$_3$)$_2$ | Isobutyl |
| CH$_2$CH$_2$CH$_2$CH$_2$NHi-Pr | Isobutyl |
| CH$_2$CH$_2$CH$_2$CH$_2$NH(c-Pr)$_2$ | Isobutyl |
| CH$_2$C(═O)N(CH$_3$)$_2$ | Isobutyl |
| CH$_2$CH$_2$C(═O)N(CH$_3$)$_2$ | Isobutyl |
| CH$_2$CH$_2$CH$_2$NHC(═NH) NH$_2$ | Isobutyl |
| CH$_2$CH$_2$CH$_2$NHC(═NH) NHCH$_3$ | Isobutyl |
| CH$_2$CH$_2$CH$_2$NHC(═NCN) NH$_2$ | Isobutyl |
| CH$_2$CH$_2$CH$_2$NHC(═NCN)NHCH$_3$ | Isobutyl |
| CH$_2$CH$_2$CH$_2$NHC(═NH)N(CH$_3$)$_2$ | Isobutyl |
| CH$_2$CH$_2$CH$_2$NHC(═NCN)N(CH$_3$)$_2$ | Isobutyl |
| CH$_2$CH$_2$CH$_2$NHC(═NCN) N(CH$_2$CH$_3$)$_2$ | Isobutyl |
| CH$_2$NH$_2$ | 2-hydroxyisobutyl |
| CH$_2$N(CH$_3$)$_2$ | 2-hydroxyisobutyl |
| CH$_2$CH$_2$NH$_2$ | 2-hydroxyisobutyl |
| CH$_2$CH$_2$N(CH$_3$)$_2$ | 2-hydroxyisobutyl |
| CH$_2$CH$_2$CH$_2$NH$_2$ | 2-hydroxyisobutyl |
| CH$_2$CH$_2$CH$_2$N(CH$_3$)$_2$ | 2-hydroxyisobutyl |
| CH$_2$CH$_2$CH$_2$CH$_2$NH$_2$ | 2-hydroxyisobutyl |
| CH$_2$CH$_2$CH$_2$CH$_2$NHCH$_3$ | 2-hydroxyisobutyl |
| CH$_2$CH$_2$CH$_2$CH$_2$N(CH$_3$)$_2$ | 2-hydroxyisobutyl |
| L-CH$_2$CH$_2$CH$_2$CH$_2$NH$_2$ | 2-hydroxyisobutyl |
| L-CH$_2$CH$_2$CH$_2$CH$_2$N(CH$_3$)$_2$ | 2-hydroxyisobutyl |
| CH$_2$CH$_2$CH$_2$CH$_2$N(CH$_2$CH$_3$)$_2$ | 2-hydroxyisobutyl |
| CH$_2$CH$_2$CH$_2$CH$_2$NH(i-Pr) | 2-hydroxyisobutyl |
| CH$_2$CH$_2$CH$_2$CH$_2$NH(c-Pr) | 2-hydroxyisobutyl |
| CH$_2$C(═O)NHCH$_3$ | 2-hydroxyisobutyl |
| CH$_2$C(═O)N(CH$_3$)$_2$ | 2-hydroxyisobutyl |
| CH$_2$CH$_2$C(═O)NH$_2$ | 2-hydroxyisobutyl |
| CH$_2$CH$_2$C(═O)N(CH$_3$)$_2$ | 2-hydroxyisobutyl |
| CH$_2$CH$_2$CH$_2$NHC(═NH)NH$_2$ | 2-hydroxyisobutyl |
| CH$_2$CH$_2$CH$_2$NHC(═NH)NHCH$_3$ | 2-hydroxyisobutyl |
| CH$_2$CH$_2$CH$_2$NHC(═NCN)NH$_2$ | 2-hydroxyisobutyl |
| CH$_2$CH$_2$CH$_2$NHC(═NCN)NHCH$_3$ | 2-hydroxyisobutyl |
| CH$_2$CH$_2$CH$_2$NHC(═NH)N(CH$_3$)$_2$ | 2-hydroxyisobutyl |
| CH$_2$CH$_2$CH$_2$NHC(═NCN)N(CH$_3$)$_2$ | 2-hydroxyisobutyl |
| CH$_2$CH$_2$CH$_2$NHC(═NCN) N(CH$_2$CH$_3$)$_2$ | 2-hydroxyisobutyl |

The compounds of the invention can be prepared, isolated or obtained by any method apparent to those of skill in the art. Exemplary methods of preparation are described in detail in the examples below.

According to a feature of the present invention compounds of formula (I) may be prepared by the cyclization of a compound of formula (II):

(II)

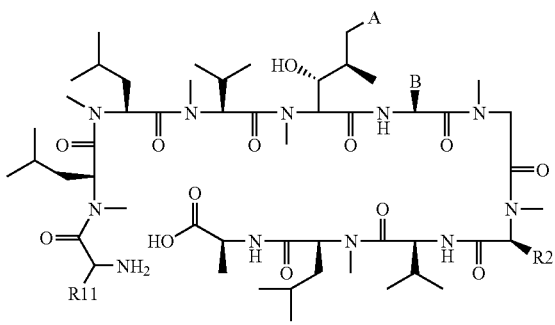

wherein A, B and $R^2$ are as defined above, $R^{11}$ is as defined for $R^1$ above or, where the group $R^3$ forming part of $R^1$ represents —$NR^4R^5$, one of the groups $R^4$ and $R^5$ may be replaced by a protecting group. The cyclization is generally performed in the presence of a coupling reagent (such as propylphosphonic anhydride or 1-ethyl-3-(3-dimethylaminopropyl)carbodiimide hydrochloride) and a base (such as 4-dimethylaminopyridine). It may be necessary to protect any amino group forming part of $R^1$ in this reaction, using a protecting group. Suitable protecting groups include tert-butyloxycarbonyl (hereafter referred to as BOC), carboxybenzyl, acetyl, tosyl, 9-fluorenylmethylcarbamate (Fmoc), benzyl, benzoyl and formyl. The reaction is generally performed at room temperature in the presence of an aprotic solvent (such as dichloromethane). Once the reaction has been performed the protecting group may be removed under normal conditions [e.g. in the case of BOC using trifluoroacetic acid (either neat or in a solvent such as dichloromethane)] or hydrochloric acid, in a solvent such as methanol. The reaction may be carried out under conditions as described in J. Org. Chem. 1990, Volume 55, page 2903.

Compounds of formula (II) may be prepared by the basic hydrolysis of a compound of formula (III):

(III)

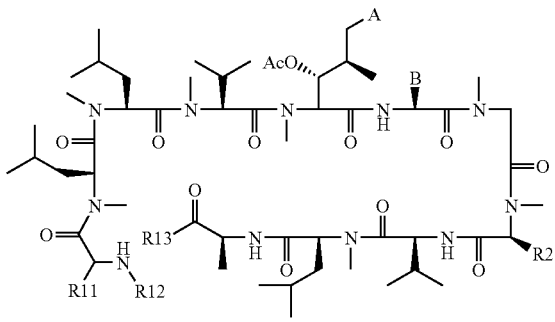

wherein A, B, $R^2$ and $R^{11}$ are as defined above, $R^{12}$ is a protecting group and $R^{13}$ is a leaving group. The hydrolysis is achieved using a base such as sodium hydroxide. $R^{12}$ is a protecting group that may be removed under basic conditions (e.g. Fmoc). $R^{13}$ is a leaving group that may be hydrolyzed under basic conditions (e.g. alkoxy, thioalkyl or thioaralkyl, preferably thiobenzyl). The reaction may be carried out under conditions as described in J. Org. Chem. 1994, Volume 59, page 7256.

Compounds of formula (III) may be prepared by the reaction of a compound of formula (IV):

(IV)

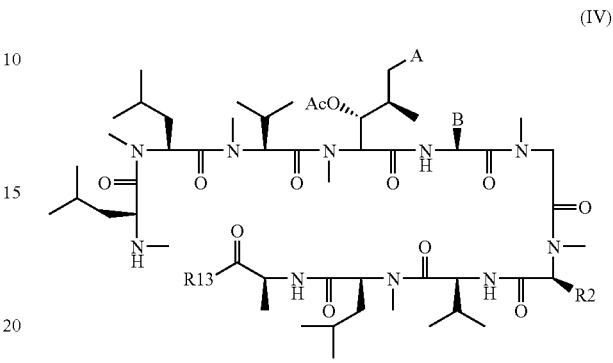

wherein A, B, $R^2$ and $R^{13}$ are as defined above, with a compound of formula (V):

(V)

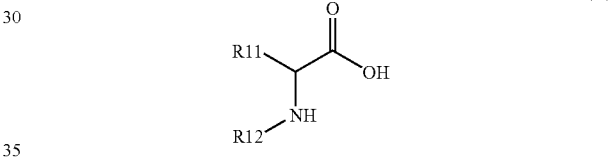

wherein $R^{11}$ and $R^{12}$ are as defined above. The reaction is generally performed in the presence of a carboxyl activating agent, e.g. a diimide such as N,N'-dicyclohexylcarbodiimide, N,N'-diisopropylcarbodiimide or (preferably) 1-ethyl-3-(3-dimethylaminopropyl)carbodiimide hydrochloride. The reaction may be carried out under conditions as described in J. Org. Chem. 1994, Volume 59, page 7255. Compounds of formula (V) are known or may be prepared by known methods.

Compounds of formula (IV) may be prepared by the acidic hydrolysis of a compound of formula (VI):

(VI)

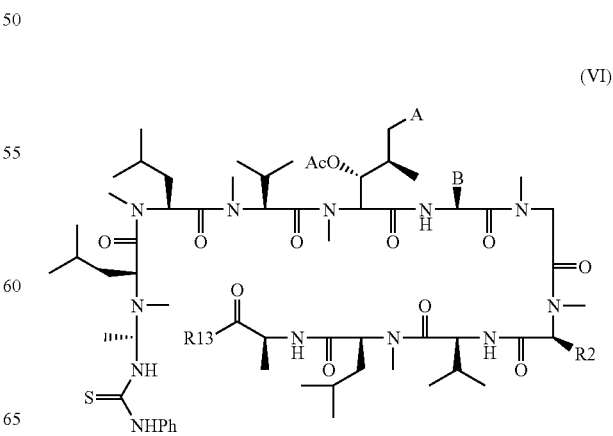

wherein A, B, $R^2$ and $R^{13}$ are as defined above and Ph is phenyl. Suitable acids for performing the acid hydrolysis include hydrochloric acid and trifluoroacetic acid. Suitable reaction conditions are described in J. Org. Chem. 1994, Volume 59, page 7255.

Compounds of formula (VI) may be prepared by the reaction of a compound of formula (VII):

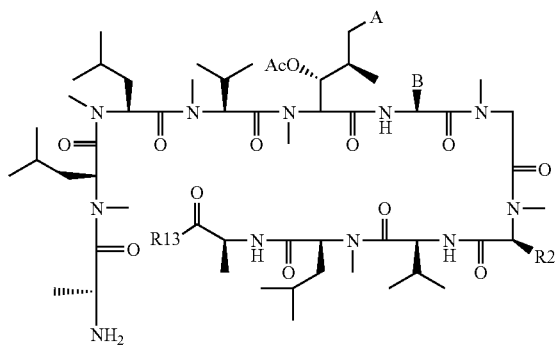

(VII)

wherein A, B, $R^2$ and $R^{13}$ are as defined above with phenyl isothiocyanate. The reaction may be carried out under conditions as described in J. Org. Chem. 1994, Volume 59, page 7255. This reaction is known to those skilled in the art as an Edman degradation. Compounds of formula (VII) above in which $R^{13}$ represents alkoxy may be prepared by interconversion of the corresponding compound of formula (VII) in which $R^{13}$ represents —$SR^{14}$ and $R^{14}$ represents alkyl or aralkyl. This can be achieved by the application or adaptation of methods described in the literature, for example see J. Med. Chem. 2006, Volume 49, page 2876.

Compounds of formula (VII) above in which $R^{13}$ represents —$SR^{14}$ and $R^{14}$ represents alkyl or aralkyl may be prepared by the ring opening of a compound of formula (VIII):

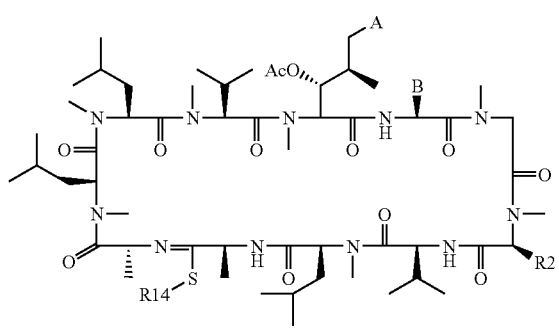

(VIII)

wherein A, B, $R^2$ and $R^{14}$ are as defined above. The reaction is generally performed using an acid, such as hydrochloric acid, in a solvent (e.g. acetonitrile). The reaction may be carried out under conditions as described in J. Org. Chem. 1994, Volume 59, page 7255.

Compounds of formula (VIII) may be prepared by the reaction of a compound of formula (IX):

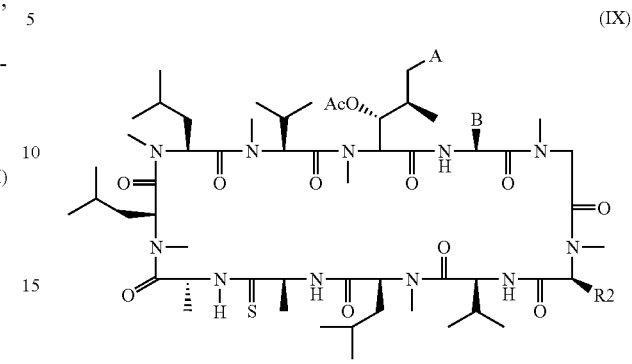

(IX)

wherein A, B and $R^2$ are as defined above, with a aralkyl halide of formula $R^{14}$—X, wherein $R^{14}$ is as defined above and X is halogen. $R^{14}$ is preferably benzyl and X is preferably bromine. The reaction is generally carried out under conditions as described in J. Org. Chem. 1994, Volume 59, page 7255.

Compounds of formula (IX) may be prepared by the reaction of a compound of formula (X):

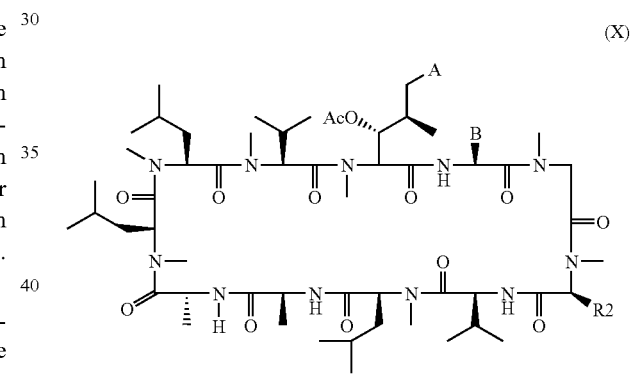

(X)

wherein $R^2$ is as defined above, with a thionation reagent. Preferably the thionation reagent is Lawesson's reagent [2,4-bis(4-methoxyphenyl)-1,3,2,4-dithiadiphosphetane-2,4-disulfide]. The reaction may be performed as described in J. Org. Chem. 1994, Volume 59, page 7254.

Compounds of formula (X) are known from the literature, for example see Are compounds of formula (X) known in the literature, for example see Helv. Chim. Acta 1982, Volume 65, page 1655-1677, or may be prepared by the adaptation of known methods Compounds of formula (I) above may be prepared by conversion of other compounds of formula (I) and this forms a further feature of the present invention. For example, compounds of formula (I) above in which $R^1$ includes a group $R^3$ and $R^3$ is a primary amine, can be converted into the corresponding compound of formula (I) in which $R^3$ is a tertiary amine via reductive amination with an appropriate aldehyde and sodium cyanoborohydride.

As discussed above, a cyclosporine compound of the invention can be in a neutral form, or in a salt form. The salt form can be any salt form known to those of skill in the art.

Particularly useful salt forms are those that are coordinated with phosphate, citrate, acetate, chloride, methanesulfonate or propionate.

Where a compound of the present invention, e.g. a compound of the invention, is substituted with a basic moiety, an acid addition salt can be formed. The acid which can be used to prepare an acid addition salt includes preferably that which produces, when combined with the free base, a pharmaceutically acceptable salt, that is, a salt whose anion is non-toxic to a subject in the pharmaceutical doses of the salt. Pharmaceutically acceptable salts within the scope of the invention are those derived from the following acids: mineral acids such as hydrochloric acid, hydrobromic acid, sulfuric acid, phosphoric acid, sulfamic acid and nitric acid; and organic acids such as acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethane-sulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids.

The corresponding acid addition salts include hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo [2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

According to a further feature of the invention, acid addition salts of the compounds of this invention can be prepared by reaction of the free base with the appropriate acid, by the application or adaptation of known methods. For example, the acid addition salts of the compounds of this invention can be prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention, e.g. compounds of the invention, can be regenerated from the salts by the application or adaptation of known methods. For example, parent compounds of the invention can be regenerated from their acid addition salts by treatment with an alkali, e.g., aqueous sodium bicarbonate solution or aqueous ammonia solution.

Where a compound of the invention, e.g. a compound of the invention, is substituted with an acid moiety, base addition salts can be formed. Pharmaceutically acceptable salts, including for example alkali and alkaline earth metal salts, within the scope of the invention are those derived from the following bases: sodium hydride, sodium hydroxide, potassium hydroxide, calcium hydroxide, magnesium hydroxide, aluminum hydroxide, lithium hydroxide, zinc hydroxide, barium hydroxide, and organic amines such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylenediamine, chloroprocaine, diethanolamine, procaine, N-benzylphenethylamine, N-methylglucamine piperazine, tris(hydroxymethyl)-aminomethane, tetramethylammonium hydroxide, and the like.

Metal salts of compounds of the present invention, e.g. compounds of the invention, can be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention, e.g. compounds of the invention, can be obtained by contacting an amine in an aqueous or organic solvent with the free acid form of the compound. Suitable aqueous solvents include water and mixtures of water with alcohols such as methanol or ethanol, ethers such as tetrahydrofuran, nitrites, such as acetonitrile, or ketones such as acetone. Amino acid salts may be similarly prepared.

The base addition salts of the compounds of this invention, e.g. compounds of the invention, can be regenerated from the salts by the application or adaptation of known methods. For example, parent compounds of the invention can be regenerated from their base addition salts by treatment with an acid, e.g., hydrochloric acid.

Pharmaceutical Compositions and Methods of Administration

The cyclosporine compounds used in the method of the present invention are preferably provided using pharmaceutical compositions containing at least one compound of general formula (I), if appropriate in the salt form, either used alone or in the form of a combination with one or more compatible and pharmaceutically acceptable carriers, such as diluents or adjuvants, or with another anti-HCV agent. In clinical practice the cyclosporine compounds of the present invention may be administered by any conventional route, in particular orally, parenterally, rectally or by inhalation (e.g. in the form of aerosols). The cyclosporine compounds of the present invention are preferably administered orally.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In a preferred embodiment, a composition of the invention is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of the invention, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions of the invention can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions or single unit dosage forms are sterile and in suitable form for administration to a subject, preferably an animal subject, more preferably a mammalian subject, and most preferably a human subject.

A pharmaceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms of the invention will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms of the invention comprise a compound of the invention, or a pharmaceutically acceptable salt, solvate or hydrate thereof lie within the range of from about 0.1 mg to about 1000 mg per day, given as a single once-a-day dose in the morning but preferably as divided doses throughout the day taken with food. Particular dosage forms of the invention have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active cyclosporine.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In preferred embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

Parenteral Dosage Forms

Although solid, anhydrous oral dosage forms are preferred, the present invention also provides parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are preferably sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical & Mucosal Dosage Forms

Although solid, anhydrous oral dosage forms are preferred, the present invention also provides transdermal, topical, and mucosal dosage forms. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Methods of Treating or Preventing HCV and/or HIV Infection in a Subject

The present invention provides methods of using a compound or composition of the invention for the treatment or prevention of a retroviral infection in a subject in need thereof. The methods generally comprise the step of administering to the subject an effective amount of the compound or composition to treat or prevent the retroviral infection. In preferred embodiments, the retroviral infection is HCV infection or HIV infection, or HCV and HIV co-infection.

In certain embodiments of the invention, the subject can be any subject infected with, or at risk for infection with, HCV. Infection or risk for infection can be determined according to any technique deemed suitable by the practitioner of skill in the art. Particularly preferred subjects are humans infected with HCV.

The HCV can be any HCV known to those of skill in the art. There are at least six genotypes and at least 50 subtypes of HCV currently known to those of skill in the art. The HCV can be of any genotype or subtype known to those of skill. In certain embodiments, the HCV is of a genotype or subtype not yet characterized. In certain embodiments, the subject is infected with HCV of a single genotype. In certain embodiments, the subject is infected with HCV of multiple subtypes or multiple genotypes.

In certain embodiments, the HCV is genotype 1 and can be of any subtype. For instance, in certain embodiments, the HCV is subtype 1a, 1b or 1c. It is believed that HCV infection of genotype 1 responds poorly to current interferon therapy. Methods of the present invention can be advantageous for therapy of HCV infection with genotype 1.

In certain embodiments, the HCV is other than genotype 1. In certain embodiments, the HCV is genotype 2 and can be of any subtype. For instance, in certain embodiments, the HCV is subtype 2a, 2b or 2c. In certain embodiments, the HCV is genotype 3 and can be of any subtype. For instance, in certain embodiments, the HCV is subtype 3a, 3b or 10a. In certain embodiments, the HCV is genotype 4 and can be of any subtype. For instance, in certain embodiments, the HCV is subtype 4a. In certain embodiments, the HCV is genotype 5 and can be of any subtype. For instance, in certain embodiments, the HCV is subtype 5a. In certain embodiments, the HCV is genotype 6 and can be of any subtype. For instance, in certain embodiments, the HCV is subtype 6a, 6b, 7b, 8b, 9a or 11a. See, e.g., Simmonds, 2004, *J Gen Virol.* 85:3173-88; Simmonds, 2001, *J. Gen. Virol.*, 82, 693-712, the contents of which are incorporated by reference in their entirety.

In certain embodiments of the invention, the subject has never received therapy or prophylaxis for HCV infection. In further embodiments of the invention, the subject has previously received therapy or prophylaxis for HCV infection. For instance, in certain embodiments, the subject has not responded to HCV therapy. Indeed, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for HCV infection but has failed show a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding. Since the compounds of the present invention act by mechanism other than current HCV therapy, it is believed that compounds of the invention should be effective in treating such nonresponders.

In certain embodiments, the subject is a subject that discontinued HCV therapy because of one or more adverse events associated with the therapy. In certain embodiments, the subject is a subject where current therapy is not indicated. For instance, certain therapies for HCV are associated with neuropsychiatric events. Interferon (IFN)-alpha plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, the present invention provides methods of treating or preventing HCV infection in subjects where the risk of neuropsychiatric events, such as depression, contraindicates treatment with current HCV therapy. The present invention also provides methods of treating or preventing HCV infection in subjects where a neuropsychiatric event, such as depression, or risk of such indicates discontinuation of treatment with current HCV therapy. The present invention further provides methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects are include bone marrow suppression, neutropenia and thrombocytopenia. Furthermore, ribavirin is toxic to red blood cells and is associated with hemolysis. Accordingly, the present invention also provides methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments the subject has received HCV therapy and discontinued that therapy prior to administration of a method of the invention. In further embodiments, the subject has received therapy and continues to receive that therapy along with administration of a method of the invention. The methods of the invention can be co-administered with other therapy for HCV according to the judgment of one of skill in the art. In advantageous embodiments, the methods or compositions of the invention can be co-administered with a reduced dose of the other therapy for HCV.

In certain embodiments, the present invention provides methods of treating a subject that is refractory to treatment with interferon. For instance, in some embodiments, the subject can be a subject that has failed to respond to treatment with one or more agents selected from the group consisting of interferon, interferon α, pegylated interferon α, interferon plus ribavirin, interferon α plus ribavirin and pegylated interferon α plus ribavirin. In some embodiments, the subject can be a subject that has responded poorly to treatment with one or more agents selected from the group consisting of interferon, interferon α, pegylated interferon α, interferon plus ribavirin, interferon α plus ribavirin and pegylated interferon α plus ribavirin.

In further embodiments, the present invention provides methods of treating HCV infection in subjects that are pregnant or might get pregnant since current therapy is also contraindicated in pregnant women.

In certain embodiments, the methods or compositions of the invention are administered to a subject following liver transplant. Hepatitis C is a leading cause of liver transplantation in the U.S. and many subjects that undergo liver transplantation remain HCV positive following transplantation. The present invention provides methods of treating such recurrent HCV subjects with a compound or composition of the invention. In certain embodiments, the present invention provides methods of treating a subject before, during or following liver transplant to prevent recurrent HCV infection.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, World J Gastroenterol 8:577-57. The methods of the invention can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, J Infect Dis 179:1254-1258. Advantageously, compounds of the invention have been shown to suppress HIV in HIV subjects. See, e.g., U.S. Pat. Nos. 5,977,067; 5,994,299, 5,948,884 and 6,583,265 and PCT publication nos. WO99/32512, WO99/67280, the contents of which are hereby incorporated by reference in their entireties. Thus, in certain embodiments, the present invention provides methods of treating or preventing HIV infection and HCV infection in subjects in need thereof.

Dosage and Unit Dosage Forms

In human therapeutics, the doctor will determine the posology which he considers most appropriate according to a preventive or curative treatment and according to the age, weight, stage of the infection and other factors specific to the subject to be treated. Generally, doses are from about 1 to about 1000 mg per day for an adult, or from about 5 to about 250 mg per day or from about 10 to 50 mg per day for an adult. In certain embodiments, doses are from about 5 to about 400 mg per day, and more preferably 25 to 200 mg per day per adult. Dose rates of from about 50 to about 500 mg per day are also preferred.

In further aspects, the present invention provides methods of treating or preventing HIV and/or HCV infection in a subject by administering, to a subject in need thereof, an effective amount of a compound of the invention, or a pharmaceutically acceptable salt thereof, with a high therapeutic index against HIV and/or HCV. The therapeutic index can be measured according to any method known to those of skill in the art, such as the method described in the examples below. In certain embodiments, the therapeutic index is the ratio of a concentration at which the compound is toxic, to the concentration that is effective against HIV and/or HCV. Toxicity can be measured by any technique known to those of skill including cytotoxicity (e.g. $IC_{50}$ or $IC_{90}$) and lethal dose (e.g. $LD_{50}$ or $LD_{90}$). Likewise, effective concentrations can be measured by any technique known to those of skill including effective concentration (e.g. $EC_{50}$ or $EC_{90}$) and effective dose (e.g. $ED_{50}$ or $ED_{90}$). Preferably, similar measurements are compared in the ratio (e.g. $IC_{50}/EC_{50}$, $IC_{90}/EC_{90}$, $LD_{50}/ED_{50}$ or $LD_{90}/ED_{90}$). In certain embodiments, the therapeutic index can be as high as 2.0, 5.0, 10.0, 15.0, 20.0, 25.0, 50.0, 75.0, 100.0, 125.0, 150.0 or higher.

The amount of the compound or composition of the invention which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions of the invention, the dosage administered to a subject is typically 0.140 mg/kg to 3 mg/kg of the subject's body weight, based on weight of the active compound. Preferably, the dosage administered to a subject is between 0.20 mg/kg and 2.00 mg/kg, or between 0.30 mg/kg and 1.50 mg/kg of the subject's body weight.

In general, the recommended daily dose range of a composition of the invention for the conditions described herein lie within the range of from about 0.1 mg to about 1000 mg per day, given as a single once-a-day dose or as divided doses throughout a day. In one embodiment, the daily dose is administered twice daily in equally divided doses. Specifically, a daily dose range should be from about 10 mg to about 200 mg per day, more specifically, between about 10 mg and about 150 mg per day, or even more specifically between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition of the invention are also encompassed by the above described dosage amounts and dose frequency schedules. Further, when a subject is administered multiple dosages of a composition of the invention, not all of the dosages need be the same. For example, the dosage administered to the subject may be increased to improve the prophylactic or therapeutic effect of the composition or it may be decreased to reduce one or more side effects that a particular subject is experiencing.

In a specific embodiment, the dosage of the composition of the invention or a composition of the invention, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition of the invention or a composition of the invention administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition of the invention followed by one or more maintenance doses. In such embodiments, the loading dose can be, for instance, about 60 to about 400 mg per day, or about 100 to about 200 mg per day for one day to five weeks. The loading dose can be followed by one or more maintenance doses. Each maintenance does can be, independently, about from about 10 mg to about 200 mg per day, more specifically, between about 25 mg and about 150 mg per day, or even more specifically between about 25 and about 80 mg per day. Maintenance doses are preferably administered daily and can be administered as single doses, or as divided doses.

In certain embodiments, a dose of a compound or composition of the invention can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition of the invention is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations of about 1200 to about 8000 ng/mL, or about 2000 to about 4000 ng/mL for one to five days. Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, the present invention provides unit dosages comprising a compound of the invention, or a pharmaceutically acceptable salt thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

Combination Therapy

The present invention provides methods of treatment of prevention that comprise the administration of a second agent effective for the treatment or prevention of HCV and/or HIV infection in a subject in need thereof. The second agent can be any agent known to those of skill in the art to be effective for the treatment or prevention of the HCV and/or HIV infection. The second agent can be a second agent presently known to those of skill in the art, or the second agent can be second agent later developed for the treatment or prevention of HCV and/or HIV. In certain embodiments, the second agent is presently approved for the treatment or prevention of HCV and/or HIV.

In certain embodiments, a compound of the invention is administered in combination with one second agent. In further embodiments, a second agent is administered in combination with two second agents. In still further embodiments, a second agent is administered in combination with two or more second agents.

Suitable second agents include small-molecule, orally bioavailable inhibitors of the HCV enzymes, nucleic-acid-based agents that attack viral RNA, agents that can modulate the host immune response. Exemplary second agents include: (i) current approved therapies (peg-interferon plus ribavirin), (ii) HCV-enzyme targeted compounds, (iii) viral-genome-targeted therapies (e.g., RNA interference or RNAi), and (iv) immunomodulatory agents such as ribavirin, interferon (INF) and Toll-receptor agonists.

In certain embodiments, the second agent is a modulator of the NS3-4A protease. The NS3-4A protease is a heterodimeric protease, comprising the amino-terminal domain of the NS3 protein and the small NS4A cofactor. Its activity is essential for the generation of components of the viral RNA replication complex.

One useful NS3-4A protease inhibitor is BILN 2061 (Ciluprevir; Boehringer Ingelheim), a macrocyclic mimic of peptide product inhibitors. Although clinical trials with BILN 2061 were halted (preclinical cardiotoxicity), it was the first NS3 inhibitor to be tested in humans. See Lamarre et al., 2003, Nature 426:186-189, the contents of which are hereby incorporated by reference in their entirety.

Another useful NS3-4A protease inhibitor is VX-950 (Vertex/Mitsubishi), a protease-cleavage-product-derived peptidomimetic inhibitor of the NS3-4A protease. It is believed to be stabilized into the enzyme's active site through a ketoamide. See, e.g., Lin et al., 2005, J. Biol. Chem. Manuscript M506462200 (epublication); Summa, 2005, Curr. Opin. Investig. Drugs. 6:831-7, the contents of which are hereby incorporated by reference in their entireties.

In certain embodiments, the second agent is a modulator of the HCV NS5B The RNA-dependent RNA polymerase (RdRp). Contained within the NS5B protein, RdRp synthesizes RNA using an RNA template. This biochemical activity is not present in mammalian cells.

One useful modulator of RdRp is NM283 (Valopicitabine; Idenix/Novartis). NM283, is an oral prodrug (valine ester) of NM107 (2'-C-methyl-cytidine) in phase II trials for the treatment or prevention of HCV infection. See, e.g., U.S. Patent Application Publication No. 20040077587, the contents of which are hereby incorporated by reference in their entirety.

Other useful modulators of RdRp include 7-deaza nucleoside analogs. For instance, 7-Deaza-2'-C-methyl-adenosine is a potent and selective inhibitor of hepatitis C virus replication with excellent pharmacokinetic properties. Olsen et al., 2004, Antimicrob. Agents Chemother. 48:3944-3953, the contents of which are hereby incorporated by reference in their entirety.

In further embodiments, the second agent is a non-nucleoside modulator of NS5B. At least three different classes of non-nucleoside inhibitors (NNI) of NS5B inhibitors are being evaluated in the clinic.

Useful non-nucleoside modulators of NS5B include JTK-003 and JTK-009. JTK-003 has been advanced to phase II. Useful non-nucleoside modulators of NS5B include the 6,5-fused heterocyclic compounds based on a benzimidazole or indole core. See, e.g., Hashimoto et al., WO 00147883, the contents of which are hereby incorporated by reference in their entirety.

Further useful polymerase NNIs include R803 (Rigel) and HCV-371, HCV-086 and HCV-796 (ViroPharma/Wyeth). Additional useful NNIs include thiophene derivatives that are reversible allosteric inhibitors of the NS5B polymerase and bind to a site that is close to, but distinct from, the site occupied by benzimidazole-based inhibitors. See, e.g., Biswal, et al., 2005, J. Biol. Chem. 280, 18202-18210 (2005).

Further useful NNIs for the methods of the invention include benzothiadiazines, such as benzo-1,2,4-thiadiazines. Derivatives of benzo-1,2,4-thiadiazine have been shown to be highly selective inhibitors of the HCV RNA polymerase. Dhanak, et al., 2002, J. Biol. Chem. 277:38322-38327, the contents of which are hereby incorporated by reference in their entirety.

Further useful NNIs for the methods of the invention, and their mechanisms, are described in LaPlante et al., 2004 Angew Chem. Int. Ed. Engl. 43:4306-4311; Tomei et al., 2003, J. Virol. 77:13225-13231; Di Marco et al., 2005, J. Biol. Chem. 280:29765-70; Lu, H., WO 2005/000308; Chan et al., 2004, Bioorg. Med. Chem. Lett. 14:797-800; Chan et al., 2004, Bioorg. Med. Chem. Lett. 14:793-796; Wang et al., 2003, J. Biol. Chem. 278:9489-9495; Love, et al., 2003, J. Virol. 77:7575-7581; Gu et al., 2003, J. Biol. Chem. 278: 16602-16607; Tomei et al., 2004, J. Virol. 78:938-946; and Nguyen et al., 2003, Antimicrob. Agents Chemother. 47:3525-3530; the contents of each are hereby incorporated by reference in their entireties.

In a further embodiment, the second agent is an agent that is capable of interfering with HCV RNA such as small inhibitory RNA (siRNA) or a short hairpin RNA (shRNA) directed to an HCV polynucleotide. In tissue culture, siRNA and vector-encoded short hairpin RNA shRNA directed against the viral genome, effectively block the replication of HCV replicons. See, e.g., Randall et al., 2003, Proc. Natl. Acad. Sci. USA 100:235-240, the contents of which are hereby incorporated by reference in their entirety.

In a further embodiment, the second agent is an agent that modulates the subject's immune response. For instance, in certain embodiments, the second agent can be a presently approved therapy for HCV infection such as an interferon (IFN), a pegylated IFN, an IFN plus ribavirin or a pegylated IFN plus ribavirin. Preferred interferons include IFNα, IFNα2a and IFNα2b, and particularly pegylated IFNα2a (PEGASYS®) or pegylated IFNα2b (PEG-INTRON®).

In a further embodiment, the second agent is a modulator of a Toll-like receptor (TLR). It is believed that TLRs are targets for stimulating innate anti-viral response. Suitable TLRs include, bur are not limited to, TLR3, TLR7, TLR8 and TLR9. It is believed that toll-like receptors sense the presence of invading microorganisms such as bacteria, viruses and parasites. They are expressed by immune cells, including macrophages, monocytes, dendritic cells and B cells. Stimulation or activation of TLRs can initiate acute inflammatory responses by induction of antimicrobial genes and pro-inflammatory cytokines and chemokines.

In certain embodiments, the second agent is a polynucleotide comprising a CpG motif. Synthetic oligonucleotides containing unmethylated CpG motifs are potent agonists of TLR-9. Stimulation of dendritic cells with these oligonucleotides results in the production of tumour necrosis factor-alpha, interleukin-12 and IFN-alpha. TLR-9 ligands are also potent stimulators of B-cell proliferation and antibody secretion. One useful CpG-containing oligonucleotide is CPG-10101 (Actilon; Coley Pharmaceutical Group) which has been evaluated in the clinic.

Another useful modulator of a TLR is ANA975 (Anadys). ANA975 is believed to act through TLR-7, and is known to elicit a powerful anti-viral response via induction and the release of inflammatory cytokines such as IFN-alpha.

In another embodiment, the second agent is Celgosivir. Celgosivir is an alpha-glucosidase I inhibitor and acts through host-directed glycosylation. In preclinical studies, celgosivir has demonstrated strong synergy with IFNα plus ribavirin. See, e.g., Whitby et al., 2004, Antivir Chem Chemother. 15(3):141-51. Celgosivir is currently being evaluated in a Phase II monotherapy study in chronic HCV patients in Canada.

Further immunomodulatory agents, and their mechanisms or targets, are described in Schetter & Vollmer, 2004, Curr. Opin. Drug Discov. Dev. 7:204-210; Takeda et al., 2003, Annu. Rev. Immunol. 21:335-376; Lee et al., 2003, Proc. Natl. Acad. Sci. USA 100:6646-6651; Hosmans et al., 2004, Hepatology 40 (Suppl. 1), 282A; and U.S. Pat. No. 6,924,271; the contents of each are hereby incorporated by reference in their entireties.

In certain embodiments, the present invention provides methods of administering a cyclosporine derivative of the invention in combination with a second agent effective for the treatment or prevention of HIV infection. The second agent can be any agent known to those of skill in the art to be effective for the treatment of HIV infection. The second agent can be presently known or later developed.

In certain embodiments, the second agent of the invention can be formulated or packaged with the cyclosporine derivatives of the invention. Of course, the second agent will only be formulated with the cyclosporine derivative of the present invention when, according to the judgment of those of skill in the art, such co-formulation should not interfere with the activity of either agent or the method of administration. In certain embodiment, the cyclosporine derivative of the invention and the second agent are formulated separately. They can be packaged together, or packaged separately, for the convenience of the practitioner of skill in the art.

The dosages of the second agents are to be used in the combination therapies of the invention. In certain embodiments, dosages lower than those which have been or are currently being used to prevent or treat HCV infection are used in the combination therapies of the invention. The recommended dosages of second agents can obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR) 57$^{th}$ Ed., 2003, Medical Economics Co., Inc., Montvale, N.J., which are incorporated herein by reference in its entirety.

In various embodiments, the therapies (e.g., the cyclosporine derivative of the invention and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patent visit.

In certain embodiments, the cyclosporine derivative of the invention and the second agent are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least 1 day, 2 days, 3 days, 5 days, 10 days, 15 days, 30 days, 45 days, 2 months, 75 days, 3 months, or 6 months.

In certain embodiments, a cyclosporine derivative of the invention and a second agent are administered to a patient, preferably a mammal, more preferably a human, in a sequence and within a time interval such that the cyclosporine derivative can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the cyclosporine derivative and the second active agent exert their effect at times which overlap. Each second active agent can be administered separately, in any appropriate form and by any suitable route. In other embodiments, the cyclosporine derivative is administered before, concurrently or after administration of the second active agent.

In various embodiments, the cyclosporine derivative and the second agent are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other embodiments, the cyclosporine derivative and the second agent are administered concurrently.

In other embodiments, the cyclosporine derivative and the second agent are administered at about 2 to 4 days apart, at about 4 to 6 days apart, at about 1 week part, at about 1 to 2 weeks apart, or more than 2 weeks apart.

In certain embodiments, the cyclosporine derivative and the second agent are cyclically administered to a patient. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improve the efficacy of the treatment.

In certain embodiments, the cyclosporine derivative and the second active agent are administered in a cycle of less than about 3 weeks, about once every two weeks, about once every 10 days or about once every week. One cycle can comprise the administration of a cyclosporine derivative and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the cyclosporine derivative can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or, more preferably, synergistically with the cyclosporine derivative. In one embodiment, a cyclosporine derivative is administered concurrently with one or more second agents in the same pharmaceutical composition. In another embodiment, a cyclosporine derivative is administered concurrently with one or more second agents in separate pharmaceutical compositions. In still another embodiment, a cyclosporine derivative is administered prior to or subsequent to administration of a second agent. The invention contemplates administration of a cyclosporine derivative and a second agent by the same or different routes of administration, e.g., oral and parenteral. In certain embodiments, when a cyclosporine derivative is administered concurrently with a second agent that potentially produces adverse side effects including, but not limited to, toxicity, the second active agent can advantageously be administered at a dose that falls below the threshold that the adverse side effect is elicited.

Kits

The invention also provides kits for use in methods of treatment or prophylaxis of HCV infection. The kits can include a pharmaceutical compound or composition of the invention and instructions providing information to a health care provider regarding usage for treating or preventing a bacterial infection. Instructions may be provided in printed form or in the form of an electronic medium such as a floppy disc, CD, or DVD, or in the form of a website address where such instructions may be obtained. A unit dose of a compound or composition of the invention can include a dosage such that when administered to a subject, a therapeutically or prophylactically effective plasma level of the compound or composition can be maintained in the subject for at least 1 day. In some embodiments, a compound or composition of the invention can be included as a sterile aqueous pharmaceutical composition or dry powder (e.g., lyophilized) composition. In one embodiment, the compound is according to formula (I).

In some embodiments, suitable packaging is provided. As used herein, "packaging" refers to a solid matrix or material customarily used in a system and capable of holding within fixed limits a compound or composition of the invention suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Kits of the invention may also comprise, in addition to the compound or composition of the invention, second agents or compositions comprising second agents for use with compound or composition as described in the methods above.

The following Examples illustrate the synthesis of representative cyclosporine compounds used in the present invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLE 1

Formaldehyde (7.2 µL of a 37% by weight solution in water) was added to a solution of [D-Lysyl]$^8$cyclosporine (Compound 2, 50 mg) in 5.0 mL of methanol at room temperature. A 1.0 M solution of sodium cyanoborohydride in tetrahydrofuran (8.7 µL) was then added, followed by acetic acid (50 µL). The reaction mixture was stirred at room temperature overnight. The reaction mixture was then taken up into dichloromethane, washed with a saturated solution of sodium hydrogen carbonate, and dried over sodium sulphate. The resulting solution was filtered and the dichloromethane removed by evaporation. The product was then dissolved in acetonitrile and purified by high pressure column chromatography. The resulting product was then dissolved in dichloromethane, washed with a 2.0 N sodium hydroxide solution, dried over sodium sulfate, filtered and concentrated to yield [(N,N-ε-dimethyl)-D-lysyl]$^8$cyclosporine (Compound 1) as a solid. $^1$H NMR (400 MHz, CDCl$_3$) δ 2.20 (s, 6H), 7.06 (d, J=8.3 Hz, 1H), 7.49 (d, J=8.4 Hz, 1H), 7.71 (d, J=7.5 Hz, 1H), 8.08 (d, J=9.6 Hz, 1H). MS (ESI+) 1287.7.

EXAMPLE 2

Compound 2 was prepared according to method described in J. Org. Chem., 1990, Volume 55, page 2985 et. seq. [N$^ε$-(tert-Butoxycarbonyl)-D-lysyl]$^8$cyclosporine (1.0 g) in dichloromethane was cooled in an ice water bath. Trifluoroacetic acid (10 mL) was added dropwise over several minutes. After 30 minutes the reaction mixture was concentrated by evaporation of solvent, then dissolved in dichloromethane and purified by column chromatography to yield [D-Lysyl]$^8$cyclosporine (Compound 2, 803 mg) as a solid. $^1$H NMR (400 MHz, CDCl$_3$) δ 7.05 (d, J=8.2 Hz, 1H), 7.49 (d, J=8.1 Hz, 1H), 7.79 (d, J=6.9 Hz, 1H), 7.82 (d, J=9.7 Hz, 1H), 8.10 (bs, 2H). MS (ESI+) 1259.7.

[N$^ε$-(tert-Butoxycarbonyl)-D-Lysyl]$^8$cyclosporine was prepared from N$^α$-[(9-fluorenylmethyl)oxy]carbonyl-N$^ε$-(tert-butyloxycarbonyl)-D-lysyl-N-methylleucyl-N-methylleucyl-N-methylvalyl-(2S,3R,4R,6E)-3-hydroxy-4-methyl-2-(methylamino)-6-octenoyl-L-2-aminobutyrylsarcosyl-N-methylleucylvalyl-N-methylleucylalanyl benzyl ester according to the method described in J. Org. Chem., 1990, Volume 55, page 2985 et. seq.

HCV Activity

The compounds of the present invention were tested for activity against HCV using the methods adapted from those described by Kriger et al, Journal of Virology, 2001 volume 75, p. 4614-4624, Pietschmann et al, Journal of Virology, 2002 volume 76, p. 4008-4021, and using HCV RNA constructs as described in U.S. Pat. No. 6,630,343. Compounds were examined in the human hepatoma cell line ET (lub ubi neo/ET), a HCV RNA replicon containing a stable luciferase (LUC) reporter. The HCV RNA replicon ET contains the 5' end of HCV (with the HCV Internal Ribosome Entry Site (IRES) and the first few amino acids of the HCV core protein) which drives the production of a firefly luciferase (LUC), ubiquitin, and neomycin phosphotransferase (NeoR) fusion protein. Ubiquitin cleavage releases the LUC and NeoR proteins. The EMCV IRES element controls the translation of the HCV structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The activity of the LUC reporter is directly proportional to HCV replication levels and positive-control antiviral compounds produce a reproducible antiviral response using the LUC endpoint.

The compounds were dissolved in DMSO at five half-log concentrations each, ranging from either 0.03 to 3 μM or 1 to 100 μM. Subconfluent cultures of the ET line were plated out into 96 well plates dedicated for the analysis of cell numbers (cytotoxicity) or antiviral activity and the next day the compounds were added to the appropriate wells. The cells were processed 72 hours later when the cells were still subconfluent. Antiviral activity was expressed as $EC_{50}$ and $EC_{90}$, the effective concentration of compound that reduced viral replication by 50% and 90%, respectively. Compound $EC_{50}$ and $EC_{90}$ values were derived from HCV RNA levels assessed as HCV RNA replicon derived LUC activity. Cytotoxicity was expressed as $IC_{50}$ and $IC_{90}$, the concentration of compound that inhibited cell viability by 50% and 90%, respectively. Compound $IC_{50}$ and $IC_{90}$ values were calculated using a colorimetric assay as an indication of cell numbers and cytotoxicity. The activity of the LUC reporter is directly proportional to HCV RNA levels in the human cell line. The HCV-replicon assay was validated in parallel experiments using interferon-alpha-2b as a positive control. Cyclosporine was also tested by way of comparison. Compounds 1 and 2 inhibited HCV replication in human liver cells. In addition, when considering the level of cytotoxicity, compounds 1 and 2 invention exhibited a safety margin (antiviral $IC_{50}$ versus cytotoxicity $EC_{50}$).

HIV Activity

Certain compounds of the present invention were also tested for antiretroviral activity against human immunodeficiency virus-1 (HIV) using infection of the human T-lymphoblastoid cell line, CEM-SS, with the HIV strain HIV-1IIIB (Weislow et al., 1989, *J. Natl. Cancer Inst.* 81:577-586). In this MTS cytoprotection assay, each experiment included cell control wells (cells only), virus control wells (cells plus virus), drug toxicity wells (cells plus drug only), drug calorimetric control wells (drug only) as well as experimental wells (drug plus cells plus virus). Compounds were first dissolved in DMSO and tested using six half-log dilutions, starting with a high concentration of either 20 or 2 μM. HIV-1RF was added to each well in a volume of 50 μL, the amount of virus determined to give approximately 90% cell killing at 6 days post-infection. At assay termination, assay plates were stained with the soluble tetrazolium-based dye MTS (CellTiter 96 Reagent, Promega) to determine cell viability and quantify compound toxicity. MTS is metabolized by the mitochondria enzymes of metabolically active cells to yield a soluble formazan product, providing a quantitative analysis of cell viability and compound cytotoxicity. The assay was validated in parallel experiments using Zidovudine (3'-azido-3'-deoxythymidine or AZT) as a positive control. The assay included determinations of compound $EC_{50}$ (concentration inhibiting virus replication by 50%), $IC_{50}$ (concentration resulting in 50% inhibition of cell growth) and a selectivity index ($IC_{50}/EC_{50}$).

Compound 1 inhibited HIV strain HIV-1IIIB at concentrations that were not cytotoxic.

All publications and patent applications cited in this specification are herein incorporated by reference as if each individual publication or patent application were specifically and individually indicated to be incorporated by reference. While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What we claim is:

1. A method of treating or preventing hepatitis C virus infection in a subject, the method comprising administering to the subject a therapeutically effective amount of a cyclosporine derivative of formula (I):

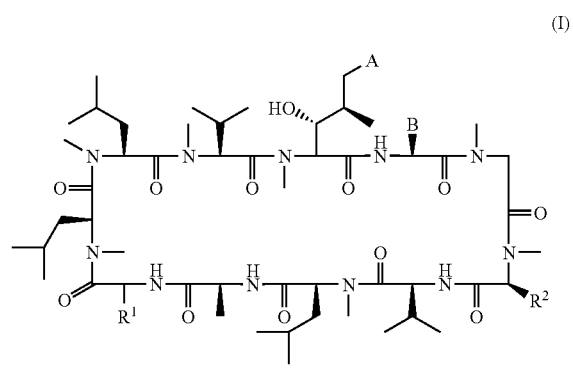

wherein:
A represents (E) —CH=CHCH$_2$R, wherein R represents hydrogen, —SH, thioalkyl, or carboxyl;
B represents methyl or ethyl;
R$^1$ represents:
straight- or branched-chain alkyl containing from one to six carbon atoms, substituted by one or more groups R$^3$ which may be the same or different;
straight- or branched-chain alkenyl or alkynyl containing from two to six carbon atoms substituted by one or more groups R$^3$ which may be the same or different;
or cycloalkyl containing from three to six carbon atoms optionally substituted by one or more groups R$^3$ which may be the same or different;
R$^2$ represents isobutyl or 2-hydroxyisobutyl;
R$^3$ is selected from the group consisting of —NR$^4$R$^5$, —C(=O)NR$^4$R$^5$ and —C(=NR$^6$)NR$^4$R$^5$;
R$^4$ and R$^5$, which may be the same or different, each represent:
hydrogen;
straight- or branched-chain alkyl containing from one to six carbon atoms;
straight- or branched-chain alkenyl or alkynyl containing from two to four carbon atoms; or
cycloalkyl containing from three to six carbon atoms optionally substituted by straight- or branched-chain alkyl containing from one to six carbon atoms;
or R$^4$ and R$^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

R$^6$ represents hydrogen, straight- or branched-chain alkyl containing from one to six carbon atoms, cyano, alkylsulfonyl, sulfonamide, or nitro;

or a pharmaceutically acceptable salt thereof;

with the proviso that when A is (E)—CH=CHCH$_3$ and B is ethyl, then R$^1$ is not L—CH$_2$CH$_2$CH$_2$NH$_2$.

2. The method according to claim 1 in which A represents (E)—CH=CHCH$_2$R, R represents hydrogen and B represents ethyl.

3. The method according to claim 1 or 2 in which R$^2$ represents isobutyl and R$^1$ is the (D) isomer.

4. The method according to claim 1 in which R$^1$ represents straight- or branched-chain alkyl containing from one to six carbon atoms, substituted by one group R$^3$.

5. The method according to claim 4 in which R$^1$ represents straight- or branched-chain alkyl containing from two to six carbon atoms, substituted by one group R$^3$.

6. The method according to claim 1 in which R$^3$ represents —NR$^4$R$^5$.

7. The method according to claim 6 in which R$^4$ and R$^5$, which may be the same or different, represent hydrogen or straight- or branched-chain alkyl containing from one to six carbon atoms.

8. The method according to claim 1 in which A represents (E)—CH=CHCH$_2$R; R represents hydrogen; B represents ethyl; R$^1$ represents straight-chain alkyl containing from one to six carbon atoms substituted by a group R$^3$; R$^2$ represents isobutyl; R$^3$ represents —NR$^4$R$^5$; and R$^4$ and R$^5$ represent hydrogen or straight- or branched-chain alkyl containing from one to six carbon atoms.

9. [(N,N-ε-Dimethyl)-D-lysyl]$^8$cyclosporine, or a pharmaceutically acceptable salt thereof.

10. A cyclosporine derivative of formula (I):

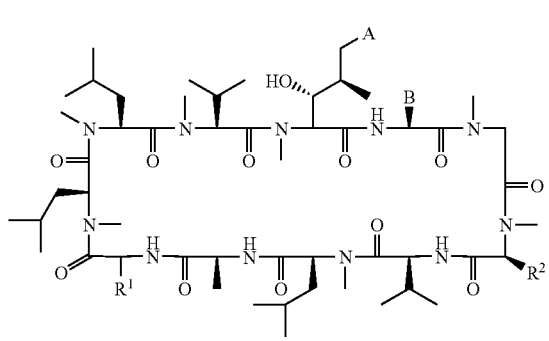

wherein:
A represents (E)—CH=CHCH$_2$R, wherein R represents hydrogen, —SH, thioalkyl, or carboxyl;
B represents methyl or ethyl;
R$^1$ represents:
straight- or branched-chain alkyl containing from one to six carbon atoms, substituted by one or more groups R$^3$ which may be the same or different;
straight- or branched-chain alkenyl or alkynyl containing from two to six carbon atoms substituted by one or more groups R$^3$ which may be the same or different;
or cycloalkyl containing from three to six carbon atoms optionally substituted by one or more groups R$^3$ which may be the same or different;
R$^2$ represents isobutyl or 2-hydroxyisobutyl;
R$^3$ is selected from the group consisting of —NR$^4$R$^5$, —C(=O)NR$^4$R$^5$ and —C(=NR$^6$)NR$^4$R$^5$;

R$^4$ and R$^5$, which may be the same or different, each represent:
hydrogen;
straight- or branched-chain alkyl containing from one to six carbon atoms;
straight- or branched-chain alkenyl or alkynyl containing from two to four carbon atoms; or
cycloalkyl containing from three to six carbon atoms optionally substituted by straight- or branched-chain alkyl containing from one to six carbon atoms;
or R$^4$ and R$^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

R$^6$ represents hydrogen, straight- or branched-chain alkyl containing from one to six carbon atoms, cyano, alkylsulfonyl, sulfonamide, or nitro;

or a pharmaceutically acceptable salt thereof;

with the proviso that (a) the cyclosporine derivative is not [D-lysyl]$^8$cyclosporine, (b) when R$^1$ is —CH$_2$R$^3$ or —CH$_2$CH$_2$R$^3$ then R$^3$ is not or —C(=O)NH$_2$, and (c) when A is (E)—CH=CHCH$_3$ and B is ethyl, then R$^1$ is not L—CH$_2$CH$_2$CH$_2$CH$_2$NH$_2$.

11. The cyclosporine derivative according to claim 10 in which A represents (E)—CH=CHCH$_2$R, R represents hydrogen and B represents ethyl.

12. The cyclosporine derivative according to claim 10 or 11 in which R$^2$ represents isobutyl and R$^1$ is the (D) isomer.

13. The cyclosporine derivative according to claim 10 in which R$^1$ represents straight- or branched-chain alkyl containing from one to six carbon atoms, substituted by one group R$^3$.

14. The cyclosporine derivative according to claim 13 in which R$^1$ represents straight- or branched-chain alkyl containing from two to six carbon atoms, substituted by one group R$^3$.

15. The cyclosporine derivative according to claim 10 in which R$^3$ represents —NR$^4$R$^5$.

16. The cyclosporine derivative according to claim 15 in which R$^4$ and R$^5$, which may be the same or different, represent hydrogen or straight- or branched-chain alkyl containing from one to six carbon atoms.

17. The cyclosporine derivative according to claim 10 in which A represents (E)—CH=CHCH$_2$R; R represents hydrogen; B represents ethyl; R$^1$ represents straight-chain alkyl containing from one to six carbon atoms substituted by a group R$^3$; R$^2$ represents isobutyl; R$^3$ represents —NR$^4$R$^5$; and R$^4$ and R$^5$ represent hydrogen or straight- or branched-chain alkyl containing from one to six carbon atoms.

18. A composition comprising a cyclosporine derivative of formula (I) as defined in claim 10, or a pharmaceutically acceptable salt thereof, in association with a pharmaceutically acceptable diluent or carrier.

19. A process for the preparation of a cyclosporine derivative of formula (I) as defined in claim 10, comprising the cyclization of a compound of formula (II):

(II)

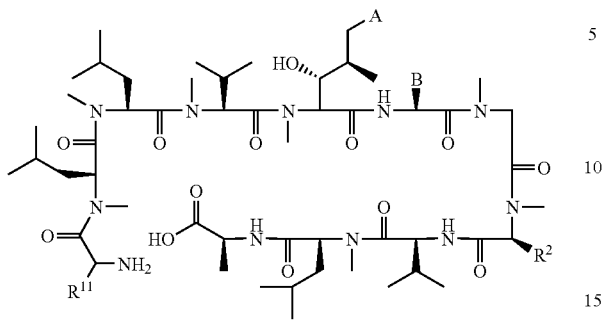

wherein A, B and $R^2$ are as defined in claim 10, $R^{11}$ is as defined for $R^1$ in claim 10, wherein one of $R^4$ or $R^5$ present in $R^{11}$ is optionally a protecting group which is removed after the cyclization of the compound of formula (II), in the presence of a coupling reagent and a base;

optionally followed by the conversion of the compound of formula (I) thus obtained into a pharmaceutically acceptable salt.

20. The process according to claim 19 in which the group $R^3$ forming part of $R^{11}$ represents —$NR^4R^5$;
  wherein one of the groups $R^4$ and $R^5$ represent:
    hydrogen;
    straight- or branched-chain alkyl containing from one to six carbon atoms;
    straight- or branched-chain alkenyl or alkynyl containing from two to four carbon atoms; or
    cycloalkyl containing from three to six carbon atoms optionally substituted by
    straight- or branched-chain alkyl containing from one to six carbon atoms; and
  the other one of the groups $R^4$ and $R^5$ is replaced by a protecting group wherein the protecting group is removed after the cyclization of the compound of formula (II).

* * * * *